United States Patent
Aardse et al.

(10) Patent No.: US 11,229,172 B2
(45) Date of Patent: Jan. 25, 2022

(54) **BOTANICAL SEED OF GARLIC, *ALLIUM SATIVUM***

(71) Applicant: De Groot en Slot B.V., Broek op Langedijk (NL)

(72) Inventors: Lennaert Crispijn Aardse, Broek op Langedijk (NL); Eduard Alphonsus Langedijk, Broek op Langedijk (NL); Martin Slot, Broek op Langedijk (NL)

(73) Assignee: De Groot en Slot B.V., Broek op Langedijk (NL)

( * ) Notice: Subject to any disclaimer, the term of this patent is extended or adjusted under 35 U.S.C. 154(b) by 0 days.

(21) Appl. No.: 16/960,984

(22) PCT Filed: Jan. 12, 2018

(86) PCT No.: PCT/EP2018/050760
§ 371 (c)(1),
(2) Date: Jul. 9, 2020

(87) PCT Pub. No.: WO2019/137616
PCT Pub. Date: Jul. 18, 2019

(65) Prior Publication Data
US 2021/0059145 A1 Mar. 4, 2021

(51) Int. Cl.
*A01H 6/04* (2018.01)
*A01H 5/06* (2018.01)

(52) U.S. Cl.
CPC .............. *A01H 6/04* (2018.05); *A01H 5/06* (2013.01)

(58) Field of Classification Search
None
See application file for complete search history.

(56) References Cited

U.S. PATENT DOCUMENTS

| 5,746,024 A | 5/1998 | Rice et al. |
| 8,987,558 B2 | 3/2015 | Cappellen et al. |

FOREIGN PATENT DOCUMENTS

| EP | 0984693 B1 | 12/2002 |
| WO | 9847371 A1 | 10/1998 |
| WO | 2013128454 A1 | 9/2013 |

OTHER PUBLICATIONS

Etoh et al. "Seed productivity and germinability of various garlic [*Allium sativum L.*] clones collected in Soviet Central Asia." Memoirs of the Faculty of Agriculture-Kagoshima University (Japan) (1988). (Year: 1988).*
Etoh et al., "Seed Productivity and Germinability of Various Garlic Clones Collected in Soviet Central Asia", Mem. Fac. Agr. Kagoshima Univ., 1988, pp. 129-139, vol. 24.
"Garlic", National Library of Medicine, https://www.ncbi.nlm.nih.gov/search/all/?term=garlic, Jun. 16, 2020, 4 pages.
"Inspection Regulations Naktuinbouw", Naktuinbouw, 2018, pp. 1-100.
Kamenetsky et al., "Garlic (*Allium sativum L.*) and its Wild Relatives from Central Asia: Evaluation for Fertility Potential", Acta Horticulture, 2004, pp. 83-91, vol. 637.
Nam et al., "Development of Multiplex RT-PCR for Simultaneous Detection of Garlic Viruses and the Incidence of Garlic Viral Disease in Garlic Genetic Resources", Plant Pathol. J., 2015, pp. 90-96, vol. 31:1.
Pooler et al., "True seed production in garlic", Sex Plant Reprod, 1994, pp. 282-286, vol. 7.
Shemesh et al., "Unlocking variability: inherent variation and development traits of garlic plants originated from sexual reproduction", Planta, 2008, pp. 1013-1024, vol. 227.

* cited by examiner

*Primary Examiner* — Charles Logsdon
(74) *Attorney, Agent, or Firm* — The Webb Law Firm

(57) ABSTRACT

Provided herein are garlic plants capable of producing substantial amounts of botanical seed, i.e. at least 500 viable seeds per garlic plant. Also provided herein is a use of the present garlic plant for the production of botanical seeds, i.e. at least 500 viable seeds per garlic plant and to seeds and plant parts obtainable from the present garlic plants. Specifically, provided herein are garlic plants capable of producing at least 500 viable seeds per garlic plant, representative seed of said garlic plant deposited under NCIMB 42869.

5 Claims, 2 Drawing Sheets

BOTANICAL SEED OF GARLIC, *ALLIUM SATIVUM*

CROSS-REFERENCE TO RELATED APPLICATION

Figure 1:
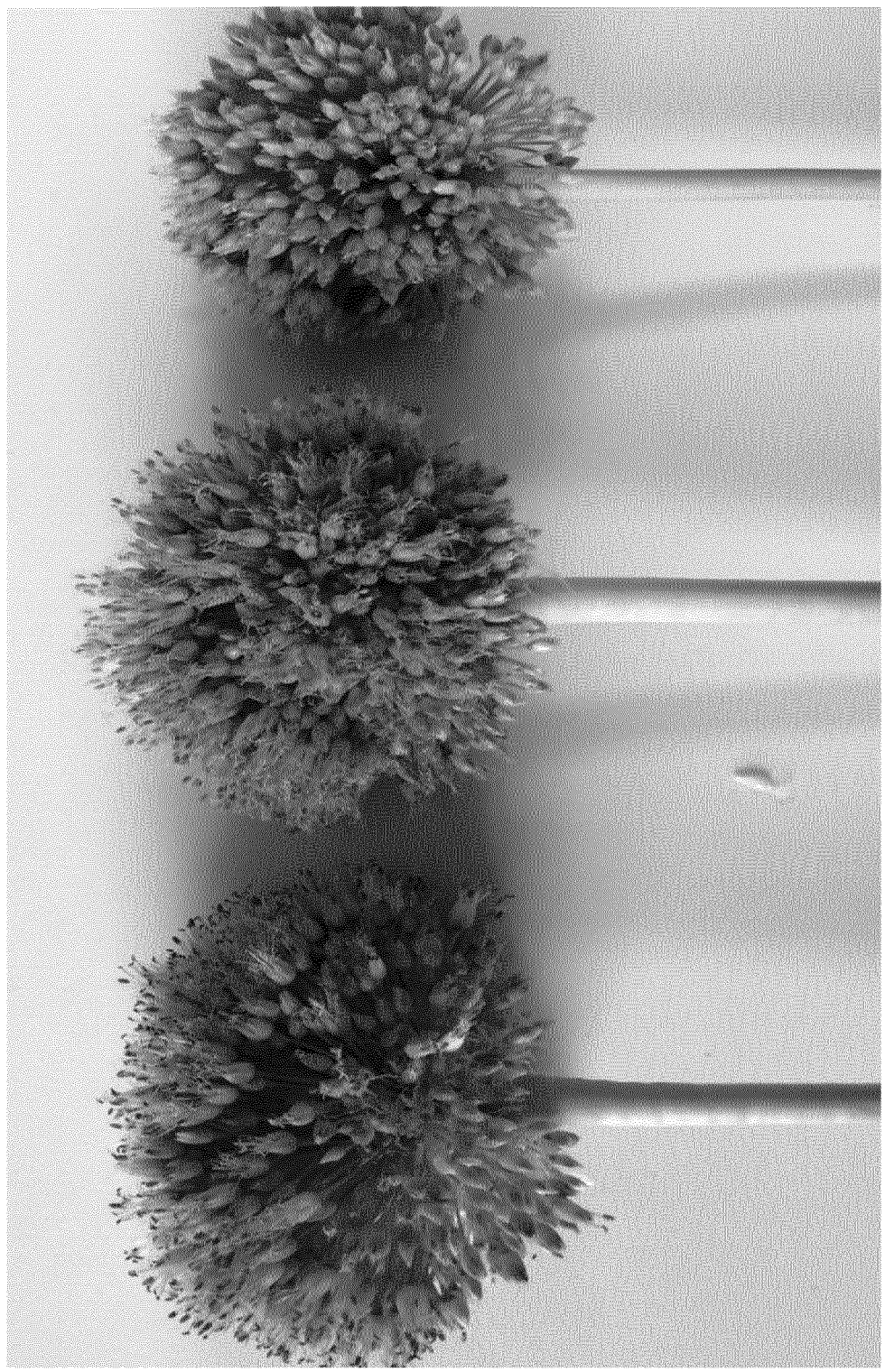

This application is the United States national phase of International Application No. PCT/EP2018/050760 filed Jan. 12, 2018, the disclosure of which is hereby incorporated by reference in its entirety.

The present invention relates garlic plants capable of producing substantial amounts of botanical seed, i.e. at least 500 viable seeds per garlic plant. The present invention further relates to use of the present garlic plant for the production of botanical seeds, i.e. at least 500 viable seeds per garlic plant and to seeds and plant parts obtainable from the present garlic plants.

Garlic, or *Allium sativum*, is a vegetable crop which is traditionally propagated by cloves, originating at the base of the adult plant.

Garlic cloves are used, raw or cooked, for their characteristic and strong flavour as seasoning or condiment of dishes. Garlic has a particular pungent flavour that softens and sweetens considerable during cooking. Another use is a medicinal application where research is aimed at the role of garlic on preventing cardiovascular diseases and on the inverse relation between garlic intake and some cancers of the digestive tract.

*Allium sativum* belongs to the family of the Amaryllidaceae, former Alliaceae, together with amongst others leek, onion and shallot. The plant originates from areas now known as Central Asia and Georgia on the Caucasus. From there the crop spread to the Mediterranean area. The perennial plant forms a bulb to store its reserves for winter. This bulb sits on top of a hard and flat ring which is covered in roots. The main bulb consists of a varying number of closely packed and curved cloves.

A 40 to 80 cm long and leafless stalk rises directly from the basal plate. At this basal part, the stalk is enclosed by leafy sheaths; at the top the umbel is located which has a long pointed spathe covering the flowers before they blossom.

However, contrary to leek, onion and shallot, no botanical seed of garlic is available for commercial sales since garlic plants have poorly developed flowers and, in so far present, these flowers are sterile. Most garlic flowering structures have an abundant number of aerial bulbs or bulbils in the flower formed, which are clones from the flower bearing plant and suppress the formation of flowers. Thus, growing seeds on garlic is hampered seriously by the presence of bulbils. Further, when these bulbils fall on the ground, new plants are established, which can be designated as clones, and not progeny, from the mother plant.

For research and breeding purposes, bulbils can be removed manually thus giving room for flowers to develop. Garlic flowers have one style and six stamen opposite the petals; the anthers and pollen can vary in color depending on the species. The ovaries are superior, and three-lobed with three locules. After pollination, a limited amount of seed can be harvested, these seeds are black with a round shape.

Garlic plants are hardy and not often affected by diseases; however, nematodes and some decay fungi attack the plant especially when it stays in the soil for longer times. Garlic may also be suffering from pink root (*Phoma terrestris*), white rot (*Sclerotium cepivorum*), downy mildew (*Peronospora destructor*), rust (*Puccinia allii*) or viruses.

In garlic 5 main types can be distinguished:
 *A. sativum* var. *longiscuspis*
 *A. sativum* var. *pekinense*
 *A. sativum* var. *subtropical*
 *A. sativum* var. *sativum*
 *A. sativum* var. *ophioscorodon*

Further, garlic types are divided in soft neck and hard neck, and colours vary between white and purple. Soft neck garlic differs from hard neck garlic in the sense that soft neck garlic plants have a bundle of leaves protruding from the bulb rather than having a central stalk as with hard neck garlic.

Identification of varieties is performed by morphological data, ecology, chemical/biochemical parameters, isozymes and molecular analysis (using e.g. RAPD/RFLP). An up to date overview of available molecular data is, for instance, available in the National Library of Medicine, National Center for Biotechnology Information database under the scarch term "Garlic". Many SNPs can be found between different races of garlic, and between garlic and other *Allium* crops.

Garlic as product is aimed at different global or regional markets; though this listing is not exhaustive, to this end the following types can be distinguished:
 violet spring garlic
 French striped garlic
 fresh white garlic
 Chinese garlic
 Castaflo garlic
 tropical garlic For quality aspects garlic bulbs and garlic cloves are assessed on many characteristics relating to yield, shape, colour, size, uniformity but also the absence of soil, bruises and visible damage by frost, insects, viruses and the like.

Main viruses which affect garlic are LYSV, GCLV, SLV and OYDV, the presence of these viruses can be checked with the use of specific qPCR markers or RT-PCR markers (Moon Nam, Yeong-Hoon Lee, Chung Youl Park, Min-A Lee, Yang-Soo Bae, Seungmo Lim, Joong Hwan Lee, Jae Sun Moon, and Su-Heon Lee (2015). Development of Multiplex RT-PCR for Simultaneous Detection of Garlic Viruses and the Incidence of Garlic Viral Disease in Garlic Genetic Resources. Plant Pathol. J. 31: 90-96).

The 2014 global production of garlic was around 25 million tonnes from which a vast majority originates from China and India. In Europe, Spain is an important garlic producer.

Since garlic is mainly propagated vegetatively, problems associated with this propagation method are many. First, there is little influx from new genetic information, resulting in a very slow adaptation to new demands as e.g. resistance to pests and disease or for agronomic traits, higher yield or quality. The year by year vegetative propagation of garlic also results in the risk that, with every year of vegetative propagation, the crop becomes increasingly infected with nematodes, viroids and viral, bacterial or fungal diseases. To ensure that vegetatively propagated garlic is free of disease, there is a schedule of classification to minimize the risk of spreading these diseases.

The NAKtuinbouw document "Inspection Regulations Naktuinbouw" describes field inspection where classes AA, A and HP are determined. In relation to virus infection, class AA is free of viruses, class A has a maximum of 0.1% infection and class HP a maximum of 0.16% infection. For mildew, nematodes and white rot only 0% infection is accepted.

Class AA may be traded as material for further propagation; class A is solely allowed for propagation inside a company and class HP is only allowed for production of garlic for consumption. Distinctive features for the different classes are summarized in table I below.

TABLE I criteria for classification of garlic cloves

| Class AA | Class A | Class HP |
|---|---|---|
| Virus 0% | Virus 0.1% | Virus 0.16% |
| Downy mildew 0% | Downy mildew 0% | Downy mildew 0% |
| Nematodes 0% | Nematodes 0% | Nematodes 0% |
| White rot 0% | White rot 0% | White rot 0% |
| Category AA can be traded as planting material for planting material cultivation | Category A can be used for own cultivation of planting material | Category HP must only be traded for the cultivation of garlic for consumption |

A similar classification scheme is used by French garlic growers, as stricter standards than described by the European Directive 93/61/EC regarding vegetable propagating and planting material.

Therefore, propagation is limited by the permission to use the cloves or bulbs for further seed material or that they are classified as product for the consumption market only. The rationale for this is, that with every cycle of propagation the cloves/bulbs produced can be infected by fungi, bacteria, nematodes and/or viruses.

The process of vegetative propagation is, next to time consuming, very expensive and labour-intensive; it is difficult to produce healthy garlic propagation material which is free or almost free of clove/bulb transmissible diseases and pests.

Next to these phytosanitary demands, the market is asking for garlic types with more diversity than the existing available varieties; preferably by supplying botanical or true garlic seed (TGS). But, until now, no hybridisation of garlic is possible due to the absence of male and good seed bearing female lines.

Production of true seed, or botanical seed, of garlic would address these problems; via breeding new genetic resources can be explored and using seeds, no problems due to successive vegetative generations would occur. This material, grown from seed, is essentially disease- and virus free, which will contribute to a good and reliable harvest of a healthy crop. Availability of seed from crosses between distinct garlic varieties can lead to a more diverse and healthy crop in which also new traits as improved disease resistances, can be introduced.

Attempts to grow botanic or true seeds on garlic are repeatedly reported. Etoh et al. (Etoh, T., Y. Noma, Y. Nishitarumizu and T. Wakamoto (1988). Seed productivity and germinability of various garlic clones collected in Soviet Central Asia. Mem. Fac. Agr. Kagoshima Univ., 24: 129-139) report the use of one fertile clone; in two years of successive seed production, in total 1,402 plants produced 22,850 seeds; that is an average of 16 seeds per plant; germination of these seeds was on average 14.6%.

Pooler and Simon (Pooler, M. R., and P. W. Simon (1994). True seed production in garlic. Sex. Plant Reprod. 7: 282-286) describe how they produced a small amount of seed on garlic flowers from which they first manually removed the vegetative top sets (or bulbils) form the inflorescence. During 5 successive years of experimentation they harvested, from approx. 1950 inflorescences, around 665 seeds, from which 63 were able to germinate. The vast majority (80-90%) of harvested seeds here appeared to be empty or shrivelled seeds. Only 5 of the 63 germinated seeds developed into bulb forming plants.

In U.S. Pat. No. 5,746,024 is described how garlic plants are cured from viruses applying e.g. tissue culture techniques. These—self-pollinated—plants reportedly then give rise to large quantities of viable seeds, where "large quantity" is defined as "at least one seed germinated per plant under sterile conditions". Bulbils were not removed from the inflorescences. Data are summarized in this patent as represented below in table II:

TABLE II data from U.S. Pat. No. 5,746,024
Comparison of true seed production

| Year | No. plants | No. seeds | Germ. seeds | Germ. conditions | % germination | Germ. seeds/plant |
|---|---|---|---|---|---|---|
| 1992* | ~500 | 320 | 49 | Sterile | 15.5% | 0.1 |
| 1991** | 10 | 361 | 233 | Sterile | 64.5 | 23.3 |
| 1995** | 53 | 1377 | 490 | Perlite | 35.6 | 9.3 |

*= results reported in literature for indicated year
**= results using the invention as described for indicated year In WO2013/128454, male sterile garlic plants are described where the genetic nature of the male sterility, however, remains unclear. According to the claims the described sterility can be either genetic (i.e. determined by the nuclear genome), cytoplasmic, cytoplasmic genetic or environmentally induced, for instance by temperature, humidity or light conditions. In this document no information is present concerning seed yield and the nature of the described male sterility is merely described by several possibilities rather than data are provided what the nature of the male sterility in the deposited material is. The claimed male sterility, of whatever nature, is used to provide hybrids, which are not characterized further. In this application no solution is presented to improve seed set in garlic, nor are data regarding seed yield available.

Considering the above, it is an object of the present invention, amongst other objects, to provide garlic plants capable of producing commercial quantities of viable garlic seed, i.e. at least 500 viable seed per garlic plant.

This object, amongst other objects, is met by providing the garlic plants as outlined in the appended claims.

Specifically, this object, amongst other objects is met by providing a garlic plant capable of producing at least 500 viable seeds per garlic plant, preferably at least 1000 viable seeds per garlic plant, wherein said viable seeds are obtainable by crossing a male sterile garlic parent plant with a male fertile garlic parent plant and wherein said garlic male sterile plant has a flowering phenotype type of at least 5 flowers per plant and a substantial absence of bulbils and/or said garlic male fertile plant has a flowering phenotype type of at least 5 flowers per plant and a substantial absence of bulbils.

To produce commercial quantities of TGS, inventors proceeded with selected garlic material as mentioned in patent EP 0 984 693 which describes the result of a hormonal treatment of garlic plants to promote flower formation with simultaneous reduction of bulbil formation. This improvement of the garlic flower opened the possibility to grow botanical or true garlic seeds. With this selected material it is possible to produce, on a small scale, viable seeds of garlic with a good germination rate.

Application of the results with this material led to improvement of seed set but also to the development of CMS parent garlic lines as described in U.S. Pat. No. 8,987,558.

Male sterile garlic material is applied as female or A line in production of seeds of garlic F1 material. F1 progeny produced according this invention are male fertile, so the described sterility is not (purely) cytoplasmic of nature.

Due to this ongoing selection of good flowering garlic plants (i.e. well-developed flowers and essentially absence of bulbils) during many years, there is clear progress in the program resulting in stable male fertile C lines (or pollinator lines) which provide a good seed set, and produce both higher quality seeds and genetically more uniform seed lots. The male sterile A line is propagated vegetatively from virus free material, under contained conditions to ascertain this virus free status; the male fertile C line is propagated by TGS. Production of the commercial suitable F1 seeds can be performed in the open field where pollination occurs by bees, bumblebees, flies and the like.

Having more parental lines available also opens the possibility of performing a versatile program of developing hybrids, while making different male and female combinations. Especially, seed can be produced in an open field with a vegetatively propagated male sterile line which is pollinated by a fertile, generative propagated male line.

According to a preferred embodiment the present garlic plant is a hybrid.

According to another preferred embodiment, the present garlic plant has a flowering phenotype of at least 5 flowers per plant and a substantial absence of bulbils as found in deposit NCIMB 42869 (a representative seed sample of a *Allium sativum* plant, with applicants' registration number 1617145, according to the present invention was deposited on Nov. 6, 2017 at the National Collections of Industrial, Food and Marine Bacteria (NCIMB), NCIMB Ltd, 25 Ferguson Building, Craibstone Estate, Bucksburn, Aberdeen, Scotland, AB21 9YA United Kingdom).

According to an especially preferred embodiment, the present flowering phenotype as found in deposit NCIMB 42869 is derived, or originates from said male fertile garlic plant and/or said male sterile garlic plant.

Preferably, the present garlic plant has a flowering phenotype type of 6 to 8 flowers per plant and a substantial absence of bulbils.

Considering the above, the present invention also relates to the present garlic plant for the production of botanical seed and to a method for producing garlic hybrid seeds, said method comprises vegetative propagation of the present garlic plant.

The present invention further relates to seeds obtainable from a garlic parental plant as defined, plant parts, such as cloves, obtainable from the present garlic parental plant and to a method for the production of botanical garlic seed the method comprises the steps of:

a) providing the present garlic plant;
b) allowing said garlic plant to produce seed;
c) harvesting said produced seed.

Figure 2:

In the example below, reference is made to figures wherein:

FIG. 1: shows a plant of the present invention showing improved flowering, with essentially no bulbils and an abundance of well-developed flowers FIG. 2: shows a flower as described in WO98/47371 with a lot of bulbils and poor flower development

EXAMPLE

Since garlic has a very poor flowering, resulting in no or a very low seed production, the crop is mainly vegetatively propagated. Due to the lack of crossings, there is little genetic variation available and due to the long period of vegetative propagation, garlic has many problems with infection of viruses and pathogens. Considering the above, it is desirable to develop a method to efficiently supply basic garlic material which is free of accumulated pathogens as viroids, viruses, bacteria, nematodes and fungi. Inventors addressed this problem by developing garlic plants which are essentially free of bulbils in the floral structure (FIG. 1). These novel plants are able to bear large quantities of true garlic seeds (TGS).

As an multiannual average, a planted garlic bulb results in 6 to 8 flowers which in total yield 2.33 grams of seeds, corresponding to ~1,280 seeds per plant (with an average seed count of 550 seeds per gram). These seeds are normal in the sense that they are not shrivelled or otherwise misshapen, germination is, after a dormancy breaking treatment, at least 60% and can be as high as 90%. In one case even 9 grams of seed (~4,400 seeds) were harvested from one plant.

TABLE III

Comparison of seed yield between ref. 7, 8, 9 and material described in this application

| Source | Seed yield/plant (assumption: 8 flowers per plant) |
| --- | --- |
| Etoh et al. | 16 |
| Pooler et al. | <1 |
| U.S. Pat No. 5,746,024 (FIG. 2) | 26 |
| This application | 1280 |

Since the availability of seed bearing plants, it was also possible to identify male sterile garlic plants. This in turn opened the possibility to develop garlic hybrids by having male and female garlic lines as parental material.

This material is essentially virus free since propagating several generations of vegetative material is avoided. Application of plants grown from essentially disease free TGS also has the advantage that less chemicals have to be applied to the growing crop.

Specific Embodiments of the Invention

In a first embodiment of the invention seeds are germinated on filter paper in continuous light with a temperature of 20° C. Germination is determined after 20-28 days.

In a second embodiment of the invention, seeds are primed and then sown in July (North Europe); seedlings are transferred to soil in October and plants develop mature bulbs in June/July of the following year. These bulbs are transferred to a suitable seed production site, where plants will flower after the winter period and seeds are harvested after flowering and seed set.

In another embodiment, the seedling gives rise to bulbs after growing to maturity and these bulbs break up in a multitude of cloves. These cloves can be used to have a further multiplication of the vegetative material and are sold as healthy starting material for production of garlic for the market.

In another embodiment of the invention, use of seeds instead of cloves results in a strong reduction of transport, storage of garlic bulbs and/or cloves.

In a further embodiment of the invention, application of seeds from essentially disease free plants avoids the use of protective chemicals to combat a range of diseases.

In yet another embodiment of the invention, less handling of material is possible, since use of seeds is far less labour intensive then the use of bulbs and/or cloves; which have to be cleaned after harvest and carefully stored.

In a further embodiment of the invention, application of doubled haploid inducing techniques, e.g. anther culture, microspore culture (from a male fertile line) or egg cell culture is used to develop parental lines; thus drastically reducing the time needed to develop such material.

In another embodiment of the invention, the possibility of genetic crosses between garlic varieties widens the genetic basis of novel varieties, resulting in e.g. improved disease resistance, yield and/or quality.

In a further embodiment, performing crosses between seed bearing garlic varieties opens the possibility to develop cultivars suitable for a specific geographic area or climatic conditions.

In yet another embodiment of the invention, availability of seed opens up the possibility of seed treatments, priming, pelleting and the like which all promote a healthy crop. The application of these seed-technological treatments adds further unique characters to the crop garlic from seed.

Seeds, in general, can be germinating late due to a mechanism called dormancy. This biological mechanism in nature prevents seeds of germination too early in a season; after a prolonged period of cold seeds are ready to germinate. In this way the emerged plantlets have no or a reduced risk of freezing. For plant growers however, dormancy is a process which also prevents timely germination when sowing seeds short after harvesting. Several treatments were developed in the past to break dormancy, among these are:

Scarification, the deliberate damaging of the seed hull so it permits transfer water and air to the embryo Stratification, keeping the seeds (eventually in soil) at low temperatures, thereby in fact mimicking winter.

Priming, the pre-germination of seeds until the point they are about to germinate. This results in an early and very uniform germination of the primed seeds; also a dormancy breaking effect is provided by this treatment.

Also, because of the rapid emergence of the crop, the need for combatting weeds is lower since the crop grown very early covers the soil sufficiently to prevent weeds from competing with the desired crop. Further, priming enables cultivation of a crop in areas with a short growing season.

Modern sowing equipment requires a round and smooth shape of seeds to ensure good sowing results. Since many seeds do not meet this requirement, techniques are developed to provide seeds with a layer of material (e.g. clay) which provide the desired shape and smoothness of the seed and also contribute to the weight of it. Seed treatments as encrusting (adding just enough material to cover irregularities in the seed skin) and pelleting (in addition, giving the seed an uniform round shape and a desired size) are enabled.

Within the context of the present invention, coating can be defined as a relatively thin layer of polymer supplied to the seed; to this polymer fungicides or insecticides can be added to protect the seed against soil borne pathogens and insect damage. Additionally, a dye can be added, giving the opportunity to check for correct drilling of the seeds. Alternatively, also other beneficial compounds can be added as micronutrients or beneficial micro-organisms promoting the growth of the young seedlings. Moreover, addition of germination promoting compounds as plant hormones is possible.

Encrusted seeds are not only covered with a polymer with or without extra substances as described above but also the seeds are provided with a smooth surface. This makes drilling easier and the added weight enables a more precise direct drilling of seeds treated this way. With pelleting the seeds are covered with more material, e.g. polymer bound clay, to produce a regularly shaped, round pellet. This pellet, besides eventually having the protecting substances described above, can be constructed in such a way that it will melt or split after water uptake. Priming: priming or pre-germination is a treatment where seeds are given enough moisture to have a onset of germination of the embryo inside the seed. This results in a faster emergence of the seedling, a higher emergence rate and better growth. It is believed that this head-start results in a good root system going down the soil early and growing faster.

All these techniques together with the unique characteristics of true garlic seeds enable a complete new and competitive way of growing healthy and more diverse garlic crops.

With availability of TGS several practical avenues to grow healthy garlic cloves are possible:
direct drilling of seeds to directly grow garlic bulbs and cloves in the field
growing young plants in a greenhouse or the like in small pots and transplanting these to the field
grow small cloves or bulbs from first generation plants grown from seed and use these for further cultivation. This material can be considered to be equivalent to AA class material from vegetative propagated material.

| Abbreviations and terms | |
|---|---|
| A line | male sterile (or female) parent line of a F1 hybrid |
| Bulbil | a tiny secondary bulb which forms in place of flowers on plants as onion, garlic and lily |
| C line | male fertile parent line of a F1 hybrid, pollinator |
| clove | a fleshy section of the garlic bulb; bulbs can be divided e.g. 4 or 6 to numerous cloves |
| CMS | cytoplasmic male sterility |
| F1 hybrid | the first filial generation of offspring of distinctly different parental types |
| GCLV | garlic common latent virus |
| LYSV | leek yellow stripe virus |
| OYDV | onion yellow dwarf virus |
| PCR | polymerase chain reaction |
| qPCR | quantitative PCR |
| RAPD | random amplification of polymorphic DNA |
| RFLP | restriction fragment length polymorphism |
| RT-PCR | real-time PCR |
| SLV | shallot latent virus |
| SNP | single nucleotide polymorphism |
| TGS | true garlic seed |

The invention claimed is:

1. A garlic plant capable of producing at least 500 viable seeds per garlic plant, representative seed of said garlic plant deposited under NCIMB 42869.

2. A method for producing garlic seeds comprising vegetatively propagating the garlic plant according to claim 1.

3. A plant part of the garlic plant according to claim 1.

4. The plant part according to claim 3, wherein said plant part is a clove.

5. A method for the production of a botanical garlic seed, the method comprises the steps of:
a) providing a garlic plant according to claim 1;
b) allowing said garlic plant to produce a seed; and
c) harvesting said produced seed.

* * * * *